US005439933A

United States Patent [19]

Patterson et al.

[11] Patent Number: 5,439,933

[45] Date of Patent: Aug. 8, 1995

[54] SCYTOPHYCIN COMPOUNDS, COMPOSITIONS AND METHODS FOR THEIR PRODUCTION AND USE

[75] Inventors: Gregory M. L. Patterson; Richard E. Moore, both of Honolulu, Hi.; Shmuel Carmeli, Newe Monosson, Israel; Charles D. Smith; Lucille H. Kimura, both of Honolulu, Hi.

[73] Assignee: University of Hawaii, Honolulu, Hi.

[21] Appl. No.: 86,247

[22] Filed: Jul. 1, 1993

Related U.S. Application Data

[62] Division of Ser. No. 770,084, Sep. 30, 1991, abandoned.

[51] Int. Cl.[6] .................. A61K 31/335; C07D 321/00

[52] U.S. Cl. .................................. 514/450; 549/267

[58] Field of Search ...................... 549/267; 514/450

[56] References Cited

U.S. PATENT DOCUMENTS

| | | | |
|---|---|---|---|
| 4,859,782 | 8/1989 | Higa et al. | 549/267 |
| 4,863,955 | 9/1989 | Moore et al. | 514/450 |
| 4,996,229 | 2/1991 | Moore et al. | 514/450 |

*Primary Examiner*—C. Warren Ivy
*Assistant Examiner*—A. A. Owens
*Attorney, Agent, or Firm*—Gray Cary Ware & Freidenrich

[57] ABSTRACT

Novel scytophycin compounds and compositions are disclosed, along with methods of making and using the new compounds. Methods for preparing the new scytophycin compounds from new strains of the blue-green algae *Scytonema ocellatum, Scytonema burmanicum* and purified cultures of the algae are also provided. The scytophycins are useful as anti-cancer agents, antifungal agents and for cell research purposes.

9 Claims, 12 Drawing Sheets

SCYTOPHYCIN COMPOUNDS, COMPOSITIONS AND METHODS FOR THEIR PRODUCTION AND USE

This is a divisional of application Ser. No. 07/770,084, filed Sep. 30, 1991, now abandoned.

FIELD OF THE INVENTION

The invention relates to biologically active compounds. In particular, the invention involves scytophycin compounds Useful for inhibiting cellular processes, together with methods for producing and using the compounds.

BACKGROUND OF THE INVENTION

Scytophycins are a class of compounds originally derived from blue green algae. Five such compounds ("scytophycins A–E") have been previously disclosed and characterized in U.S. Pat. Nos. 4,996,229 and 4,863,955.

Scytophycins A–E have been known to exhibit antineoplastic properties. Nevertheless, neoplastic disease continues to be a widespread problem and the majority of malignant neoplasms remain refractory to treatment. Thus, there is a continuing need for new antineoplastic agents useful either in treatment of human cancer or because they contribute to a general understanding of the underlying mechanisms by which malignant cells proliferate.

Scytophycins A–E also have been shown to inhibit fungal pathogens known to cause a variety of human disease conditions. In addition, fungal plant pathogens cause significant economic losses to agriculture each year. New compounds which are effective against fungal pathogens are needed to treat disease conditions which remain refractory to prior treatment techniques. It is further desirable to provide new antifungal compounds to inhibit fungal strains which may develop resistance to existing fungicides.

While the scytophycins A–E have been known to be useful as antineoplastic and antifungal agents, their modes of affecting cellular processes has not been previously described or understood. The lack of understanding about how scytophycins inhibit cellular processes has limited their use for other applications.

The study of cellular processes in normal and abnormal cells can lead to greater knowledge of disease conditions or to methods useful in manipulation of cells in a manner useful in medicine or agriculture. New chemical agents which interfere with cellular processes are useful in the study of cell structure, function, and reproduction.

For example, cytochalasins, derived from fungi, have been found to have specific effects on living cells. Numerous research studies have been conducted using cytochalasins because of their ability to disrupt cellular processes. Cytochalasin B is now known to inhibit microfilament formation by binding to the end unit of growing actin microfilaments and preventing their assembly. Cytochalasins are useful in the biotechnology industry, particularly for production of monoconal antibodies from hybridomas which are valuable tools in medicine, research and industry.

One side effect of using cytochalasin B which is sometimes undesirable is that it inhibits cellular sugar uptake. Further, there is a need for other inhibitors of microfilament formation, which are more stable, more soluble, and more potent than cytochalasin.

SUMMARY OF THE INVENTION

The present invention provides new scytophycin compounds, and methods for producing and using the compounds as antineoplastic agents, antifungal agents and as useful agents for cellular research.

The scytophycin compounds of the present invention have the following general chemical structure.

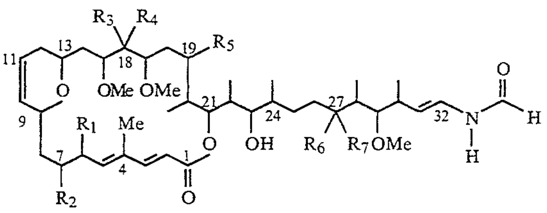

wherein:

- $R_1$ is selected from the group consisting of H and X, wherein X is selected from the group consisting of OH, OMe, $O(CH_2)_zMe$, and O—CO—Y, wherein Y is selected from the group consisting of H, $C_nH_{2n+1}$, and Ph, wherein n and z are independently selected integers from 1 to 5;
- $R_2$ is X independent of identity of X for $R_1$;
- $R_3$ is Me or $CH_2OH$ and $R_4$ is H or OH, or $R_3$ and $R_4$ together are $CH_2O$ (epoxy);
- $R_5$ is X independent of identity of X for $R_1$ and $R_2$;
- $R_6$ is OH and $R_7$ is H, or $R_6$ and $R_7$ together are O (keto);

with the provisos that:

- when $R_1$ is H, $R_2$ is OH and $R_6$ and $R_7$ are O (keto) at least one of the following limitations apply:
  - $R_3$ and $R_4$ are not $CH_2O$ (epoxy); or
  - $R_3$ is not Me; or
  - $R_5$ is not OMe; and
- when $R_1$ is H, $R_2$ is OH and $R_6$ is OH at least one of the following limitations apply:
  - $R_3$ and $R_4$ are not $CH_2O$ (epoxy); or
  - $R_5$ is not OMe.

Examples of the new scytophycins include tolytoxin, 6-hydroxyscytophycin B, 19-O-demethylscytophycin C, and 6-hydroxy-7-O-methylscytophycin E, ("the exemplary compounds") the structures of which are discussed in more detail below. The exemplary compounds can be isolated from blue-green algae (cyanobacteria) of the genus Scytonema, in particular by culturing new strains of *Scytonema ocellatum*, or *Scytonema burmanicum*, or variants thereof. Additionally, scytophycins are known to be produced in genera of blue-green algae other than Scytonema, for example Cylindrospermum. The present invention includes methods for producing scytophycins, and biologically purified cultures of the novel Scytonema strains.

The scytophycin compounds of the present invention have numerous beneficial uses which are also claimed in the present invention. The compounds are useful as antineoplastic and antifungal agents. Further, the scytophycin compounds may be used to produce useful effects in tissue-cultured cells. For example, one method of treating cells allows production of polynuclear cells. Whereas, another method of treating cells with the scytophycin compounds, surprisingly, produces enucleate cells. Researchers working in the field of cellular biology will understand that there are numerous applications for the profound effects which the new scytophycins have on cellular processes.

BRIEF DESCRIPTIONS OF THE DRAWINGS

DETAILED DESCRIPTION OF THE INVENTION

The present invention relates to new biologically active scytophycin compounds according to the following formula:

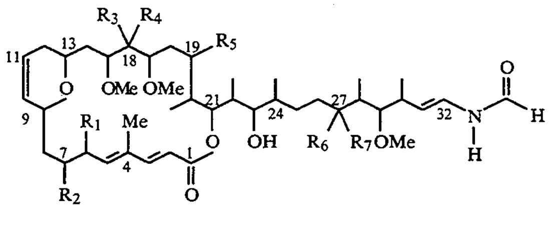

wherein:

$R_1$ is selected from the group consisting of H and X, wherein X is selected from the group consisting of OH, OMe, $O(CH_2)_zMe$, and O—CO—Y, wherein Y is selected from the group consisting of H, $C_nH_{2n+1}$, and Ph, wherein n and z are independently selected integers from 1 to 5;

$R_2$ is X independent of identity of X for $R_1$;

$R_3$ is Me or $CH_2OH$ and $R_4$ is H or OH, or $R_3$ and $R_4$ together are $CH_2O$ (epoxy);

$R_5$ is X independent of identity of X for $R_1$ and $R_2$;

$R_6$ is OH and $R_7$ is H, or $R_6$ and $R_7$ together are O (keto);

with the provisos that:

when $R_1$ is H, $R_2$ is OH and $R_6$ and $R_7$ are O (keto) at least one of the following limitations apply:

$R_3$ and $R_4$ are not $CH_2O$ (epoxy); or $R_3$ is not Me; or $R_5$ is not OMe; and when $R_1$ is H, $R_2$ is OH and $R_6$ is OH at least one of the following limitations apply:

$R_3$ and $R_4$ are not $CH_2O$ (epoxy); or $R_5$ is not OMe.

Examples of the new scytophycin compounds of the present invention include tolytoxin, 6-hydroxyscytophycin B, 19-O-demethylscytophycin C, and 6-hydroxy-7-O-methylscytophycin E, ("the exemplary compounds"), and derivatives thereof. The new scytophycins are useful as antineoplastic and antifungal agents, as well as being useful cell research tools since they are now known to inhibit microfilament formation and to be capable of producing both polynucleate and enucleate cells.

Tolytoxin, also known as 6-hydroxy-7-O-methylscytophycin B, is the major bioactive metabolite produced by *S. ocellatum*. It is also a metabolite produced by *S. burmanicum*. Based primarily on NMR data reported in Table 1 below, tolytoxin is believed to have the following chemical structure:

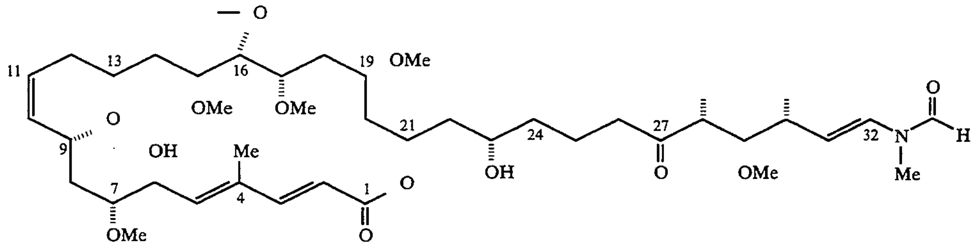

6-Hydroxyscytophycin B is a metabolite produced by *S. burmanicum*. Based primarily on NMR data reported in Table 2 below, 6-hydroxyscytophycin B is believed to have the following chemical structure:

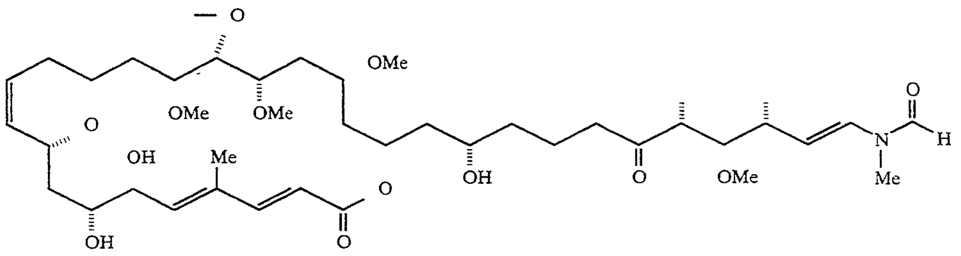

19-O-demethylscytophycin C is a metabolite produced by both *S. ocellatum* and *S. burmanicum*. Based primarily on the NMR data reported in Table 3 below, 19-O-demethylscytophycin C is believed to have the following structure:

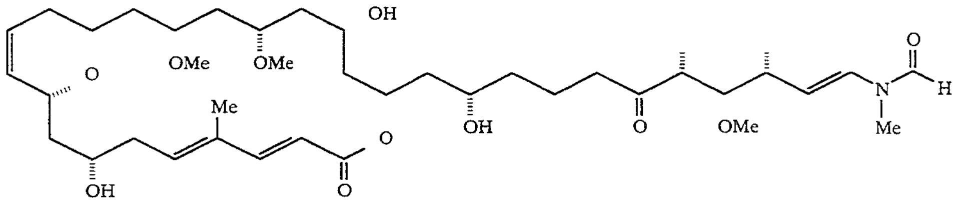

6-hydroxy-7-O-methylscytophycin E is a metabolite produced by *S. burmanicum* and is also a metabolite produced by *S. ocellatum*. Based primarily on the NMR data reported in Table 4 below, 6-hydroxy-7-O-methylscytophycin E is believed to have the following structure:

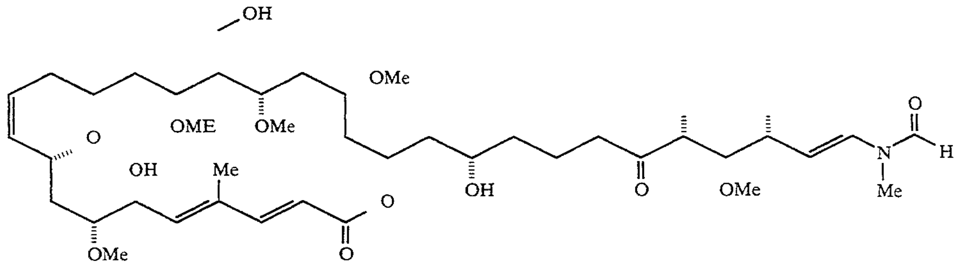

Compounds of the present invention can be produced by culturing the blue-green algae strains *Scytonema ocellatum* Lyngbye ex Bornet et Flahault (hereafter "*S. ocellatum*") and *Scytonema burmanicum* Skuja (hereafter "*S. burmanicum*").

Figure 1:
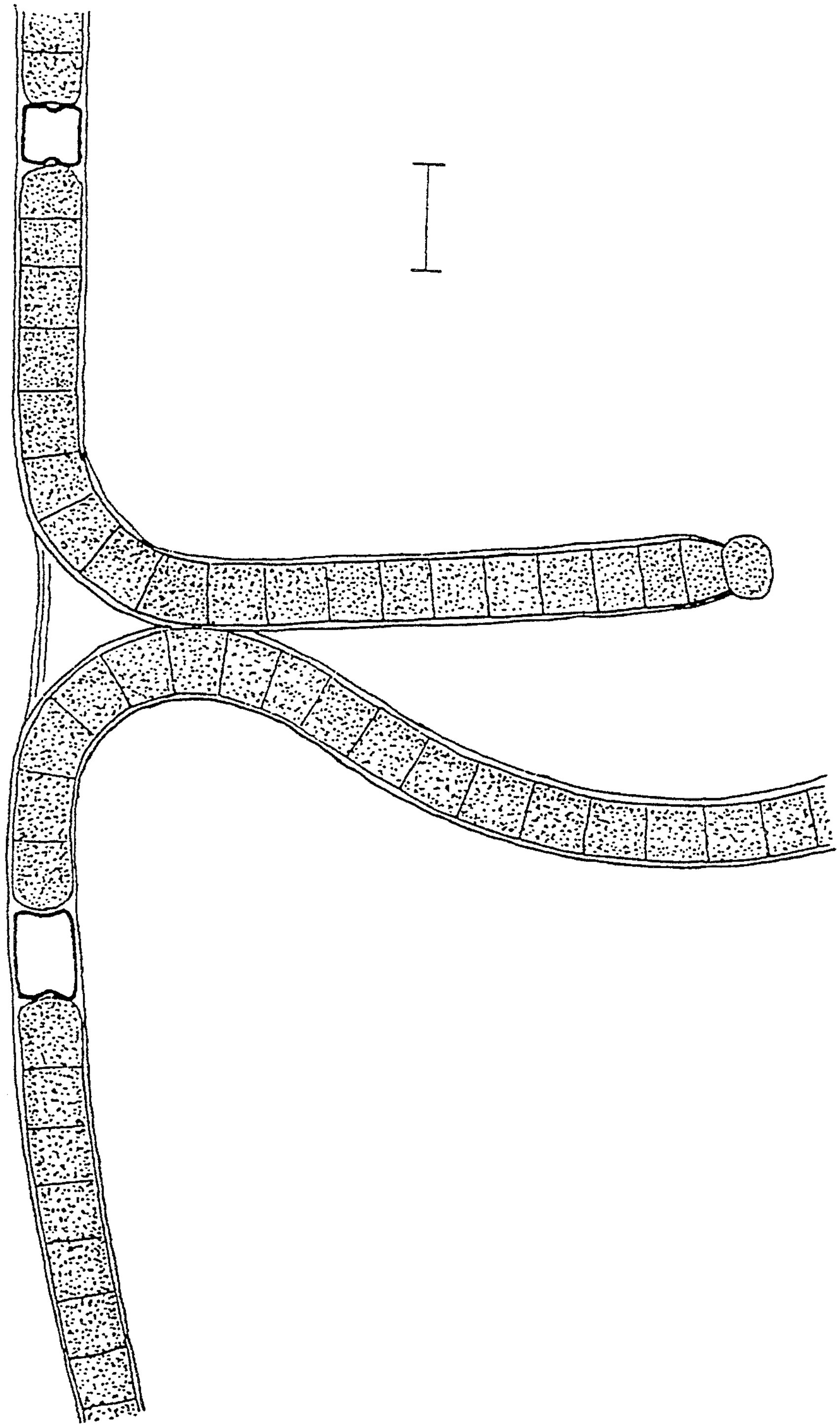
FIG. 1 is a drawing of the mature filaments of the blue-green algae strain, *Scytonema ocellatum* Lyngbye (ATCC No. 55232), which is employed in the present invention to produce new scytophycin compounds.

*S. ocellatum* has the filament structure shown in FIG. 1. The filaments typically possess geminate false branches and single intercalary heterocysts as broad as the trichomes and as long as or somewhat longer than broad. The scale bar in FIG. 1 represents 20 micrometers. As discussed in more detail below, *S. ocellatum* may be cultured to produce tolytoxin, 6-hydroxy-7-O-methylscytophycin E and 19-O-demethylscytophycin C.

Figure 2:
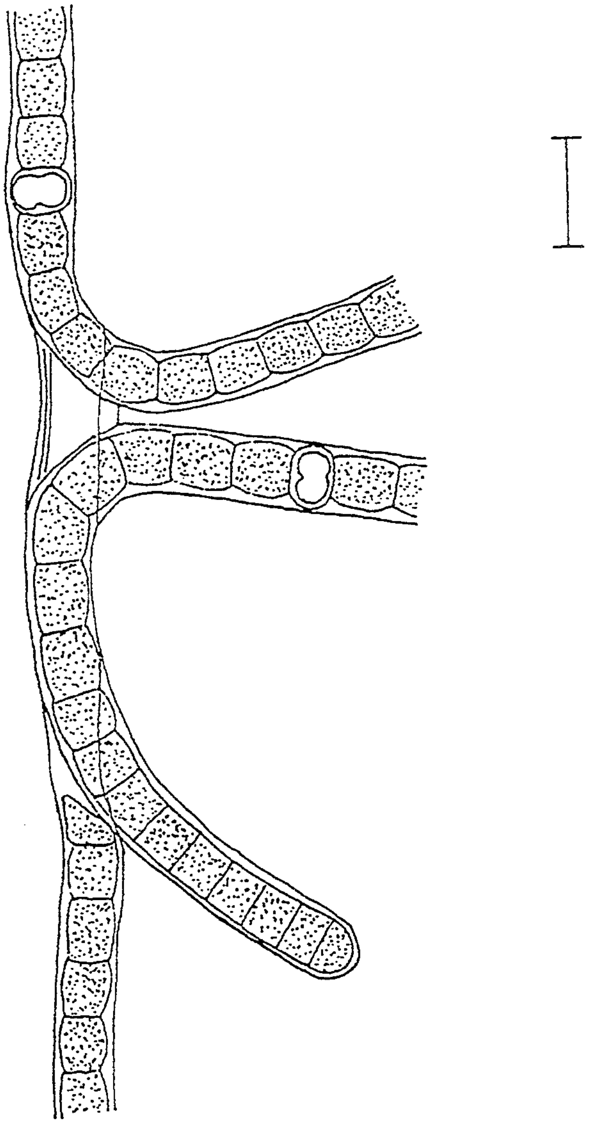
FIG. 2 is a drawing of the mature filaments of the blue-green algae strain, *Scytonema burmanicum* Skuja (ATCC No. 55231), which is employed in the present invention to produce several of the new scytophycins.
Figure 3A:
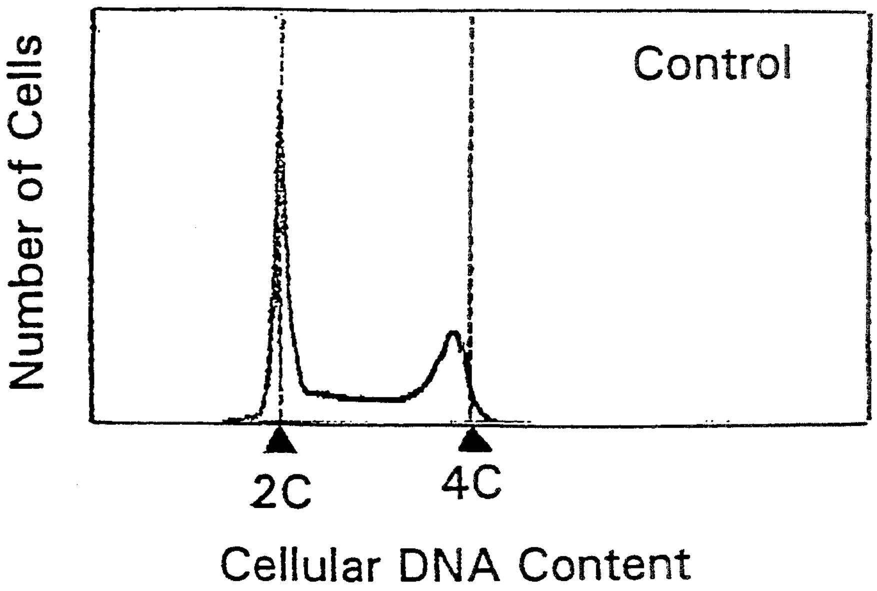
FIG. 3A–3E are a series of histograms generated by a Coulter Epics C flow cytometer demonstrating the ability of tolytoxin to produce polynuclear mammalian cells over time.
Figure 3B:
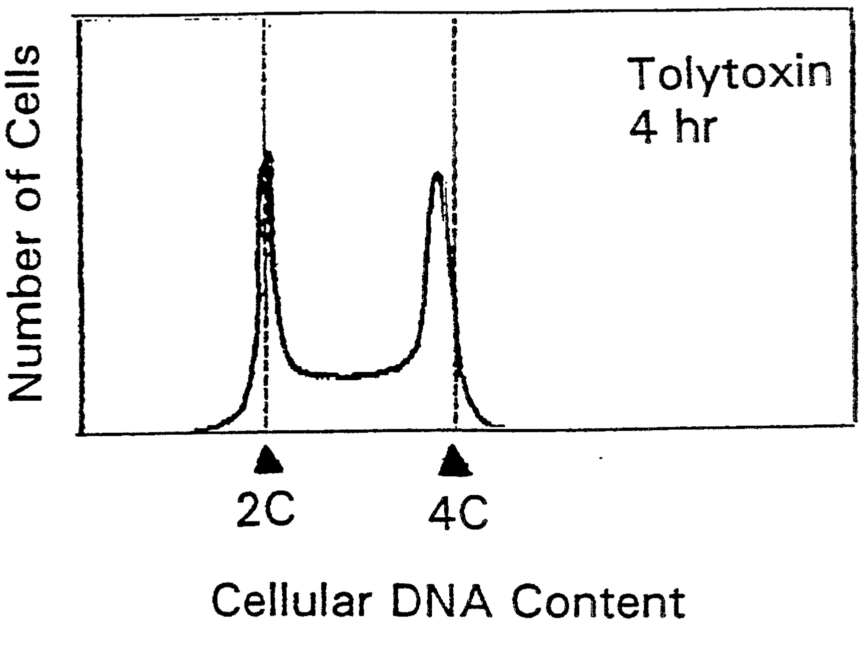
Figure 3C:
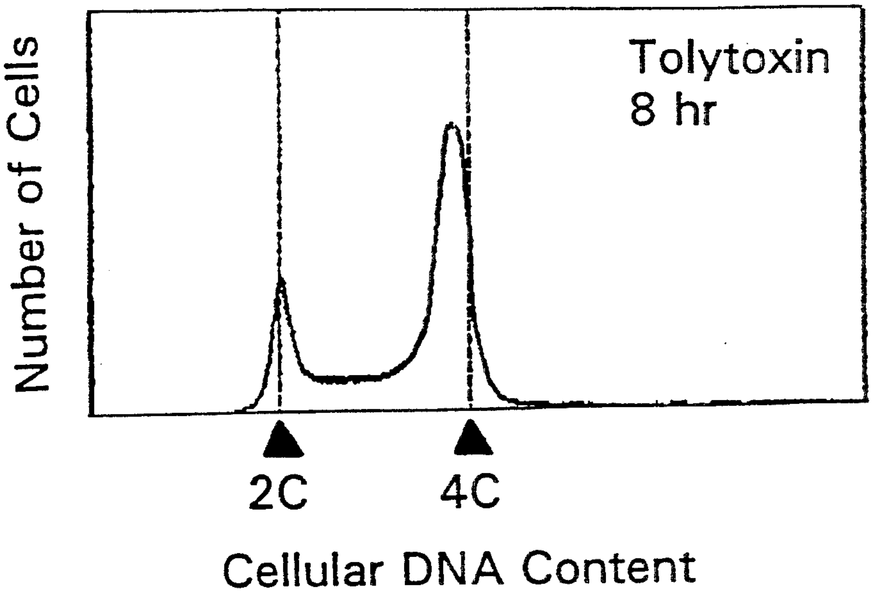
Figure 3D:
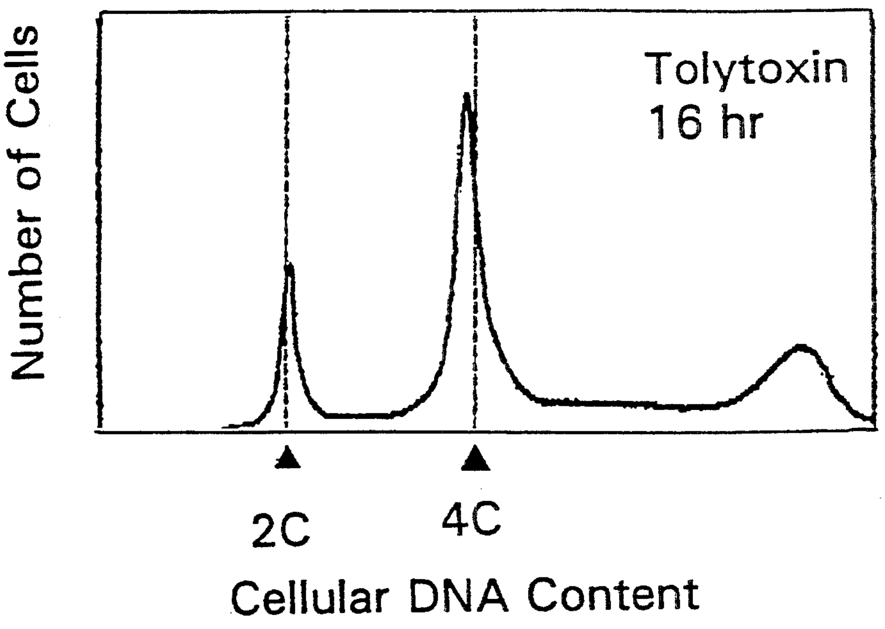
Figure 3E:
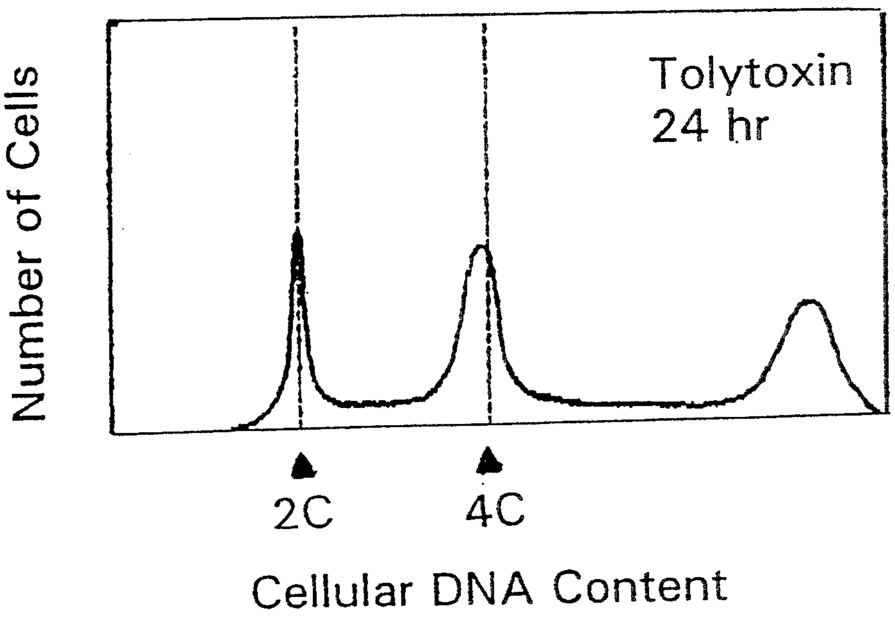

*S. burmanicum* has the filament structure shown in FIG. 2. The filaments typically have false branches which are either single or geminate. The cells are slightly constricted at the cross walls, and heterocysts are as long as broad or cylindrical. The scale bar in FIG. 2 represents 20 micrometers. As discussed in more detail below,.*S. burmanicum* may be cultured to produce tolytoxin, 6-hydroxyscytophycin B, and 6-hydroxy-7-O-methylscytophycin E and 19-O-demethylscytophycin C.

As is the case with other organisms, the characteristics of the two organisms, *S. ocellatum* and *S. burmanicum* are subject to variation. For example, recombinants, variants, or mutants of the specified strains may be obtained by treatment with various known physical and chemical mutagens, such as ultraviolet rays, X-rays, gamma rays, and N-methyl-N'-nitro-N-nitrosoguanidine. All natural and induced variants, mutants, and recombinants of the specified strains which retain the characteristic of producing a scytophycin compound are intended to be within the scope of the claimed invention.

The scytophycin compounds of the present invention can be prepared by culturing a strain of Scytonema which produces these compounds under submerged aerobic conditions in a suitable culture medium until substantial antibiotic activity is produced. Other culture techniques, such as surface growth on solidified media, can also be used to produce these compounds. The culture medium used to grow the specified strains can be any one of a number of media. Economy in production, optimal yield, and ease of product isolation are factors to consider when choosing the carbon sources and nitrogen sources to be used. Among the nutrient inorganic salts which can be incorporated in the culture media are the customary soluble salts capable of yielding iron, potassium, sodium, magnesium, calcium, ammonium, chloride, carbonate, phosphate, sulfate, nitrate, and like ions.

Essential trace elements which are necessary for the growth and development of the organisms should also be included in the culture medium. Such trace elements commonly occur as impurities in other constituents of the medium in amounts sufficient to meet the growth requirements of the organisms. It may be necessary to add small amounts (i.e. 0.2 mL/L) of an antifoam agent such as polypropylene glycol (M.W. about 2000) to large scale cultivation media if foaming becomes a problem.

For production of substantial quantities of the scytophycins, submerged aerobic cultivation in tanks can be used. Small quantities may be obtained by shake-flask culture. Because of the time lag in antibiotic production commonly associated with inoculation of large tanks with the organisms, it is preferable to use a vegetative inoculum. The vegetative inoculum is prepared by inoculating a small volume of culture medium with fragments of the vegetative trichome or heterocyst-containing form of the organism to obtain a fresh, actively growing culture of the organism. The vegetative inoculum is then transferred to a larger tank. The medium used for the vegetative inoculum can be the same as that used for larger cultivations or fermentation, but other media can also be used.

The specified organisms can be grown at temperatures between about 20° and about 30° C. The scytophycin compounds are produced at a temperature of about 25° C. and an incident illumination intensity of about 300 microEinsteins ($\mu$E)$m^{-2}sec^{-1}$. Light intensities somewhat higher or lower can also be used to produce these compounds.

As is customary in aerobic submerged culture processes of this type, carbon dioxide gas is introduced into the culture by addition to the sterile air stream bubbled through the culture medium. For efficient production of the scytophycins, the proportion of carbon dioxide should be about 1% (at 24° C. and one atmosphere of pressure).

Scytophycin production can be followed during the cultivation by testing samples of the broth against organisms known to be sensitive to these antibiotics. One useful assay organism is *Candida albicans.*

Following their production under submerged aerobic culture conditions, the scytophycin compounds can be recovered from the culture by methods used in this art. Recovery is generally accomplished by initially filtering the culture medium to separate the algal cells and then freeze drying the separated cells. The freeze dried alga can be extracted with a suitable solvent such as ethanol, methanol, isopropanol, or dichloromethane. The macrolides can be separated by subjecting this extract to rapid chromatography on reverse-phase column. The macrolides can be purified by high-performance liquid chromatography (HPLC).

As will be apparent from their structures, the scytophycins have groups which are capable of chemical modification. The derivatives which will share one or more of the biological properties of the scytophycins exemplified in the present invention include compounds having any combination of 1) a hydroxy group on C-27 in place of a keto group; 2) any combination of hydroxy and methoxy groups on C6, C-7, C-15, C-17, C-19, C-23, C-25, C-27, and C-29 ; 3) a larger alkoxy group ($C_2$–$C_6$) in place of any methoxy group; and 4) an alkanoyl ($C_1$–$C_6$) or benzoyl ester at any of the positions indicated in (1) or (2). Such derivatives of the exemplary scytophycin compounds are included in the claimed invention.

Thus, while the exemplary scytophycin compounds are known to be produced by the alga of the present invention, the other claimed compounds can be easily derivatized from the exemplary compounds using published synthetic techniques which are well known to those having ordinary skill in the art.

The compounds of the present invention can be therapeutically employed as antineoplastic or antifungal agents. Thus, a further aspect of the present invention provides compositions containing a therapeutically effective amount of at least one new scytophycin compound of the present invention, including the nontoxic addition salts thereof, which may, alone, serve to provide the above-recited therapeutic benefits. Such compositions can also be provided together with physiologically tolerable liquid, gel or solid carriers, diluents, adjuvants and excipients.

These compounds and compositions can be administered to mammals for veterinary use, such as for domestic animals, and clinical use in humans in a manner similar to other therapeutic agents. In general, the dosage required for therapeutic efficacy will vary according to the type of use and mode of administration, as well as the particularized requirements of individual hosts. Ordinarily, dosages will range from about 0.001 to 1000 $\mu$g/kg, more usually 0.01 to 100 $\mu$g/kg, of the host body weight. Alternatively, dosages within these ranges can be administered by constant infusion over an extended period of time, usually exceeding 24 hours, until the desired therapeutic benefits have been obtained.

The new scytophycin compounds may be formulated into the therapeutic compositions as neutral or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Such salts may also be formed as acid addition salts with any free cationic groups and will generally be formed with inorganic acids such as, for example, hydrochloric or phosphoric acids, or organic acids such as acetic, oxalic, tartaric, mandelic, and the like.

The suitability of particular carriers for inclusion in a given therapeautic composition depends on the preferred mode of administration. For example, antineoplastic compositions are often formulated for oral administration. Such compositions are typically prepared either as liquid solution or suspensions, or in solid forms. Oral formulations usually include such normally employed additives such as binders, fillers, carriers, preservative, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

Compositions of the present invention may also be prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Antifungal compositions are often formulated with suitable carriers for topical administration. For topical applications suitable carriers include salves, tinctures, creams, lotions, sprays, suppositories, and, in some cases, intranasal aerosols. For salves and creams, traditional binders, carriers and excipients may include, for example, polyalkylene glycols or triglycerides; such salves and creams may be formed from mixtures containing the active ingredient in the range of 0.05% to 5.0%, preferably about 0.1% to 2%.

Another aspect of the present invention relates to use of the scytophycin compounds to produce useful effects on cells growing in tissue culture. The scytophycin compounds produce effects on mammalian cells growing in cell culture which are in some ways similar to those produced by cytochalasins. (Carter, 1967, 1972). These effects are characterized by the inhibition of cell division (cytokinesis) in vitro, resulting in the production of multinucleate cells, in the inhibition of cell adhesion to substrates, and in the loss of characteristic cell shape. These effects may be observed at concentrations on the order of 1 to 5 nM for the scytophycin compounds.

The scytophycin compounds are therefore useful in the study of cell anatomy, cell function, cell reproduction, or cell physiology. Similar effects on cell division and cell morphology have been observed in mammalian cells treated with cytochalasin compounds, which effects typically require concentrations of cytochalasins on the order of 1 to 2 μM (Carter, 1967, 1972), approximately 200 to 1000 times more than the scytophycins. Thus the scytophycins constitute a significant improvement over the existing art.

At higher concentrations, or extended treatment times, treatment of tissue cultured mammalian cells with the scytophycin compounds results in extrusion of the cell nucleus from the body of the cell. Cell nuclei, once extruded, may be removed from the remainder of the cell by various physical methods, for example by aspiration into a micropipette (McGrath, U.S. Pat. No. 4,664,097) or by centrifugation, especially involving centrifugation in discontinuous density gradients, in which enucleated cells (cytoplasts) may be separated from intact cells and nuclei (Wigler and Weinstein, 1975).

The cytoplasts or the cell-free nuclei thus obtained may be used in the study of cell physiology, cell function, or cell reproduction.

In addition, the enucleated cells thus obtained may be useful in agriculture or medicine. For example, the enucleated cells may be used as hosts for transplantation of nuclei, as a method of multiplication of genetically identical organisms, as described by Prather et al. (U.S. Pat. No. 4,994,384), or for propagation of strains having desirable characteristics provided by the cytoplasm of one species combined with the nucleus or pronucleus of another species, as described by McGrath et al. (U.S., Pat. No. 4,664,097).

The enucleated cells may have desirable characteristics unrelated to propagation. For example, enucleated granulocytes are more stable when stored frozen than are normal granulocytes (Roos et al., U.S. Pat. No. 4,623,620).

The following examples serve to illustrate certain preferred embodiments and aspects of the present invention and are not to be construed as limiting the scope thereof.

Experimental

In the experimental disclosure which follows, all weights are given in kilograms (Kg), grams (g), milligrams (mg), micrograms (μg) or moles (mol). Concentrations are given as percent by volume (%), molar (M), millimolar (mM), micromolar (μM), or nanomolar (nM). Volumes are given in liters (L) or milliliters (mL). Illumination intensity is given in microEinsteins (μE). Temperatures are given in degrees Celsius (° C.). Molecular weight is abbreviated (MW). Lengths are given in meters (m), millimeters (mm), and microns (μm), unless otherwise indicated.

Throughout the specification and claims the following chemical structure abreviations are used. Me is methyl. OMe is methoxy. Ph is phenyl. OH is hydroxy. $CH_2O$ is epoxy. O is keto.

The following examples demonstrate the production, preparation, characterization and uses of the scytophycin compounds of the present invention. Exemplary compounds, tolytoxin, 19-O-demethylscytophycin C, 6-hydroxy-7-O-methylscytophycin E and 6-hydroxyscytophycin B have been isolated from *S. ocellatum* and *S. burmanicum*. The chemical Structures of the exemplary compounds have been characterized.

A number of beneficial uses have been established for the new scytophycins including antineoplastic and antifungal applications, inhibition of microfilament formation and production of polynucleate and enucleate cells.

Production of New Scytophycins

EXAMPLE 1

Exemplary compounds of the present invention were produced by cultivating new strains of blue-green algae, belonging to the genus Scytonema. *Scytonema ocellatum* was isolated from a soil sample collected at South Pasture Pond, Shawnee, Ill. The isolate was purified of contaminating blue-green algae by repeated subculture on solidified media, and was given the strain number FF-66-3. It has been deposited and made part of the stock culture collection of The American Type Culture Collection (ATCC), 12301 Parklawn Drive, Rockville, Md. 20852, under the accession number ATCC No. 55232. The ATCC deposit of *S. ocellatum* is not intended to constitute an admission that one of ordinary skill in the art could not produce the new scytophycins without undue experimentation in accordance with the methods disclosed herein. Further, no express or implied license to practice the claimed invention is created by the establishment of the ATCC deposit.

The new microorganisms were classified after comparison of their observed characteristics with published descriptions (Geitler 1932 and Desikachary 1959). Morphology was studied using an optical light microscope fitted with brightfield and phase-contrast optics. Morphological characteristics were observed on unialgal, non-axenic cultures which had been grown for at least 3 passages on an aqueous inorganic liquid medium designated A3M7 and having the: following composition:

| Ingredient | Amount |
|---|---|
| $NaNO_3$ | 200 mg/L |

-continued

| Ingredient | Amount |
|---|---|
| $NH_4Cl$ | 10 mg/L |
| $K_2HPO_4.3H_2O$ | 65 mg/L |
| $MgSO_4.7H_2O$ | 50 mg/L |
| $CaCl_2.2H_2O$ | 13 mg/L |
| 3-(N-morpholino)-propanesulfonic acid | 627 mg/L |
| Minor elements solution | 1 mL/L |
| Trace elements solution | 0.12 mL/L |

Prior to autoclaving, the pH of the complete medium was adjusted to 7 by addition of sodium hydroxide.

The composition of the minor elements solution was as follows:

| Ingredient | Amount |
|---|---|
| $FeCl_3.6H_2O$ | 0.54 g/L |
| $Na_2EDTA$ | 3.0 g/L |
| $H_3BO_3$ | 0.62 g/L |
| $MnCl_2.4H_2O$ | 1.4 g/L |
| $ZnCl_2$ | 0.10 g/L |
| $CoCl_2.6H_2O$ | 5 mg/L |
| $CuCl_2.2H_2O$ | 24 μg/L |

The composition of the trace element solution was as follows:

| Ingredient | Amount (mg/10 L of 0.1 N $H_2SO_4$) |
|---|---|
| $MoO_3$ (85%) | 176.4 |
| $NH_4VO_3$ | 229.6 |
| $Cr_2K_2(SO_4)_4.2H_2O$ | 960.2 |
| $NiSO_4.6H_2O$ | 447.8 |
| $Co(NO_3)_2.6H_2O$ | 493.8 |
| $Na_2WO_4.2H_2O$ | 179.4 |
| $Al_2(SO_4)_3$ | 317.1 |
| $As_2O_3$ | 66.1 |
| $CdCl_2$ | 81.5 |
| $SrSO_4$ | 104.9 |
| $HgCl_2$ | 67.7 |
| $PbCl_2$ | 67.1 |
| LiCl | 305.5 |
| $Rb_2SO_4$ | 78.1 |
| NaBr | 64.4 |
| KI | 65.4 |
| NaF | 110.5 |
| $Na_2SeO_4$ | 119.4 |
| $Be(NO_3)_2 \times 3\ H_2O$ | 1037.0 |

Microscopic analysis revealed that *S. ocellatum* is characterized by having false-branched filaments, 10 to 18 μm broad and several mm long. The trichome (chain of cells) ranges from 10 to 14 μm broad. Vegetative cells are quadratic or somewhat shorter than broad, and are unconstricted at the cross walls. Heterocysts are as broad as the vegetative cells and range from quadratic to cylindrical in shape. The sheath surrounding the trichome is colorless in young filaments and may become brownish and lamellated in older filaments. False branching is profuse. Branches may be short or long, and are usually geminate.

EXAMPLE 2

*S. burmanicum* was isolated from a soil sample collected at Moon Beach, Okinawa, Japan by repeated subculture on solidified media, and was given the strain number DO-4-1. It has been deposited and made part of the stock culture collection of The American Type Culture Collection, 12301 Parklawn Drive, Rockville, Md. 20852, from which it is available to the public under the accession number ATCC No. 55231. The ATCC deposit of *S. burmanicum* is not intended to constitute an admission that one of ordinary skill in the art could not produce the new scytophycins without undue experimentation in accordance with the methods disclosed herein. Further, no express or implied license to use the claimed invention is created by the establishment of the ATCC deposit.

Microscopic analysis revealed that *S. burmanicum* is characterized by having false-branched filaments, 14 to 16 μm broad. The filaments tend to be between 1–5 mm long. In unshaken liquid cultures, the filaments intertwine to form an erect cushion., portions of which extend above the level of the culture medium. The trichome is commonly 8 to 11 μm broad. Vegetative cells are quadratic or somewhat longer than broad. The cells are constricted at the cross walls in. older filaments, unconstricted in young filaments. Heterocysts are discoid to shortcylindrical, as broad as the vegetative cells or slightly broader. The sheath surrounding the cells is colorless in young filaments and may become brownish and lamellated in older filaments. False branches are solitary or geminate, relatively sparse, and variable in length.

EXAMPLE 3

The following procedures were used to produce and isolate tolytoxin, 6-hydroxy-7-O-methylscytophycin E, and 19-O-demethylscytophycin C from *S. ocellatum.* Unialgal, non-axenic cultures of *S. ocellatum* were grown in 20 L glass bottles containing the A3M7 medium described in Example 1.

Prior to autoclaving, the pH of the complete medium was adjusted to 7 with sodium hydroxide.

The cultures were illuminated continuously at an incident intensity of 300 $\mu Em^{-2}\ sec^{-1}$ from banks of cool-white fluorescent tubes and were aerated at a rate of 5 L per minute with a mixture of 0.5% (v/v) carbon dioxide in air. Following incubation at 24°±1° C. for periods averaging 30 days, the alga was harvested by filtration and then freeze dried. Yields of the lyophilized algal cells averaged 0.374 g per liter of culture.

The scytophycins were then isolated from the algal cells. Fifty grams of the freeze-dried alga was extracted three times with 3 L portions of ethanol-water (7:3, v/v), 24 hours for each extraction. The extract (9.4 g) was separated from the marc by filtration. The extract was concentrated under reduced pressure at 40° C. and applied to a flash chromatography column (YMC-GEL, ODS 120A). The chromatogram was developed with 100 mL each of the following solvents: $H_2O$, $H_2O$-methanol (1:1, 1:3, and 1:9, v/v), methanol, acetonitrile, and ethyl acetate.

Fraction 3 from the flash column [$H_2O$-methanol (1:3), 421.4 mg] was separated by preparative reversed-phase high performance liquid chromatography (Alltech Econosphere RP-18 column, 10 μm packing, 22×250 mm) using acetonitrile-methanol-water (2:1:1, v/v/v) to give 6-hydroxy-7-O-methylscytophycin E (18.0 mg), tolytoxin (161 mg), and 19-O-demethylscytophycin C (4.2 mg).

EXAMPLE 4

The following procedure was used to produce and isolate tolytoxin, 19-O-demethylscytophycin C, 6-hydroxy-7-O-methylscytophycin E and 6w-hydroxyscytophycin B from *S. burmanicum.*

Unialgal, non-axenic cultures of *S. burmanicum* were grown in 20 L glass bottles containing the aqueous inorganic medium (A3M7) of Example 1.

The cultures were illuminated continuously at an incident intensity of 300 $\mu Em^{-2}$ $sec^{-1}$ from banks of cool-white fluorescent tubes and were aerated at a rate of 5 L per minute with a mixture of 0.5% (v/v) carbon dioxide in air. Following incubation at 24°±1° C. for periods averaging 28 to 32 days, the alga was harvested by filtration and then freeze dried. Yields of the lyophilized algal cells averaged 0.220 g per liter of culture.

New scytophycin compounds were then isolated from the algal cells.. Forty-nine grams of the freeze-dried alga was extracted three times with 3 L portions of ethanol-water (7:3, v/v), 24 hours for each extraction. The extract was separated from the marc by filtration. The extract was concentrated under reduced pressure at 40° C. to give 6.2 g of material which was applied to a flash chromatography column (YMC-GEL, ODS 120A). The chromatogram was developed with 100 mL each of the following solvents: $H_2O$, $H_2O$-methanol (1:1, 1:3, and 1:9, v/v), methanol, acetonitrile, and ethyl acetate.

Fraction 3 from the flash column [$H_2O$-methanol (1:3), 151.1 mg] was further separated by preparative reversed-phase (HPLC) (Alltech Econosphere RP-18 column, 10 $\mu$m packing, 22×250 mm) using water-methanol (1:3, v/v). Seven fractions were collected having retention times of 30.5 min (2.7 mg) 34.5 (2.4), 37.5 (6.7), 41.5 (16.6), 48.0 (73.1), 61.5 (10.0), and 92.5 (3.5) . These fractions were finally purified by reversed-phase hplc with acetonitrile-methanol-water (2:1:1, v/v/v) as described above to give 6-hydroxyscytophycin B (2.9 mg) 6-hydroxy-7-O-methylscytophycin E (13.0 mg) from fraction 4, tolytoxin (50.0 mg) from fraction 5, and 19-O-demethylscytophycin C (0.7 mg) from fraction 6.

Characterization of New Scytophycins

EXAMPLE 5

Testing of tolytoxin isolated in accordance with Examples 1 and 2 above, demonstrated that it has the following characteristics:

Form: Amorphous solid.

Empirical Formula: $C_{46}H_{75}NO_{13}$

Molecular Weight: 849. MS (fast-atom bombardment): m/z 888 $(M+K)^+$, 872 $(M+Na)'^+$and 832 $(MH\text{-}H_2O)^+$. MS (electron impact): m/z 817 (M-MeOH)+. High resolution measurement: Found: m/z 817.4878. Calculated for $C_{45}H_{71}NO_{12}$: 817.4976.

CD (ethanol): $[\theta]_{297}-400$, $[\theta]_{268}+1700$, $[\theta]_{226}-3000$.

$UV\lambda_{max}$ (ethanol): 261 nm ($\epsilon$27,000)

IR (methylene chloride): 3450, 3130, 1692, 1660, 1240, 1115 $cm^{-1}$.

$H^1$ NMR: See Table 1.

$C^{13}$ NMR: See Table 1.

NMR analysis was performed on tolytoxin yielding the data reported in Table 1.

TABLE 1

| | $^1H$ AND $^{13}C$ Data for Tolytoxin | | |
|---|---|---|---|
| Position | $\delta_C$ mult. | $\delta_H$ mult, J in Hz | $^1H$-$^1H$ nOe |
| 1 | 169.10 s | | |
| 2 | 117.64 d | 5.87 d 15.8 | Me on 4 |
| 3 | 151.54 d | 7.63 d 15.8 | H-5,19 |
| 4 | 135.63 s | | |
| 4-Me | 12.40 q | 1.90 br d 1.0 | H-2,6 |
| 5 | 141.66 d | 5.96 br d 9.4 | H-3,6,7,15-OMe |
| 6 | 71.97 d | 4.38 t 9.4 | H-5,8',4-Me,7-OMe |
| 6-OH | | 4.16 br s | |
| 7 | 82.67 d | 3.48 ddd 10.9, 9.4, 1.7 | H-5,9 |
| 7-OMe | 60.33 q | 3.56 s | |
| 8 | 36.27 t | 1.30 ddd −13.8, 10.9, 2.4 | H-8',9(10) |
| | | 1.59 ddd −13.8, 9.6, 1.7 | H-6,8,13 |
| 9 | 70.62 d | 4.39 br d 9.6 | H-7,8,10 |
| 10 | 130.78 d | 5.64 ddt, 10.3, 2.8, 1.7 | H-9,11(8) |
| 11 | 124.98 d | 5.79 dddd 10.3, 5.8, 4.0, 3.0 | H-10,12,12' |
| 12 | 31.75 t | 1.90 m | H-11,13 |
| | | 1.91 m | H-11 |
| 13 | 67.03 d | 3.42 dddd 10.1,9.0,2.1,1.5 | H-8',12,15 |
| 14 | 37.01 t | 1.57 ddd −14.4, 6.4, 1.5 | CH on 16 |
| | | 1.63 ddd −14.4, 9.0, 3.2 | CH on 16, H-15 |
| 15 | 77.77 d | 3.90 dd 6.4, 3.2 | H-13,17 |
| 15-OMe | 57.37 q | 3.40 s | CH' on 16 |
| 16 | 61.21 d | | |
| $CH_2$ on | 1648.42 t | 2.77 d −4.5 | H-17 |
| | | 2.78 d −4.5 | H-14,14',15-OMe |
| 17 | 77.21 d | 3.64 dd 11.0, 4.1 | H-15, 18, 20, CH on 16 |
| 17-OMe | 54.73 q | 3.35 s | H-14 |
| 18 | 28.82 t | 1.50 ddd −14.3, 9.6, 4.1 | H-17,18',20-Me |
| | | 1.93 ddd −14.3, 11.0, 4.0 | H-19,19-OMe |
| 19 | 77.21 d | 3.37 ddd 9.6, 4.0, 1.0 | H-18',20,21 |
| 19-OMe | 57.37 q | 3.14 s | H-18' |
| 20 | 37.66 d | 2.08 ddq 9.9, 1.0, 7.0 | H-17,19,20-Me,22-Me |
| 20-Me | 9.07 q | 0.83 d 7.0 | H-18,20,21,22 |
| 21 | 76.86 d | 5.19 dd 9.9, 0.9 | H-19,22,23,23-OH 19-OMe, $H_2O$, 20-Me |
| 22 | 37.79 d | 1.92 ddq 9.9, 0.9, 6.8 | H-21,24,20-Me,22-Me |
| 22-Me | 9.07 q | 0.87 d 6.8 | H-20,22,23,24 |
| 23 | 76.36 d | 3.04 ddd 9.9, 4.3, 2.0 | H-21,24,22-Me,24-Me |
| 23-OH | | 4.04 d 4.3 | H-21 |
| 24 | 33.72 d | 1.69 dddq,9.6,3.7,2.0,6.7 | H-22,23,26',22-Me, 24-Me |
| 24-Me | 18.06 q | 0.97 d 6.7 | H-23,24,26 |

TABLE 1-continued

| Position | $\delta_C$ mult. | $^1H$ AND $^{13}C$ Data for Tolytoxin<br>$\delta_H$ mult, J in Hz | $^1$H-$^1$H nOe |
|---|---|---|---|
| 25 | 22.61 t | 1.38 m | H-25',26' |
| | | 1.76 m | H-25 |
| 26 | 41.92 t | 2.50 m | 24-Me, 28-Me |
| | | 2.55 m | H-24,25,28 |
| 27 | 213.88 s | | |
| 28 | 49.30 d | 2.76 dq 9.5, 7.0 | H-26',29-OMe |
| 28-Me | 13.47 q | 0.90 d 7.0 | H-26,28,30,29-OMe |
| 29 | 88.14 d | 3.28 dd 9.5, 2.7 | H-30 (A,B) |
| 29-OMe | 60.94 q | 3.30 s | H-28,31,28-Me,30-Me |
| 30(A) | 37.99 d | 2.45 ddq 9.2, 2.7, 7.0 | H-29,31(A),28-Me, 30-Me |
| 30(B) | 38.18 d | 2.50 ddq 9.2,2.7,7.0 | H-29,31(B),28-Me 30-Me |
| 30-Me | 19.41 q | 1.13 d 7.0 | H-30(A,B),29-OMe |
| 31(A)[a] | 111.03 d | 5.10 dd 14.0,9.2 | H-30(A), 29-OMe, NMe(A) |
| 31(B)[a] | 113.09 d | 5.16 dd.14.0, 9.2 | H-30(B), 29-OMe NME(B) |
| 32(A)[a] | 130.10 d | 6.77 d 14.0 | NCHO (A) |
| 32(B)[a] | 125.31 d | 7.09 d 14.0 | |
| NMe(A)[a] | 27.03 q | 2.98 s | H-31(A) |
| NMe(B)[a] | 33.00 q | 3.05 s | H-31(B), NCHO(B) |
| NCHO | 163.71 d | 8.34 s | H-32(A) |
| NCHO | 161.47 d | 8.09 s | NMe(B)4 |

[a]The $^1$H and $^{13}$C signals for the ene-N-methylformamide group are doubled due to restricted rotation of the N-formyl bond; (A) and (B) refer to the resulting major and minor conformers.

Based on the NMR data shown in Table 1, tolytoxin is believed to have the following chemical structure:

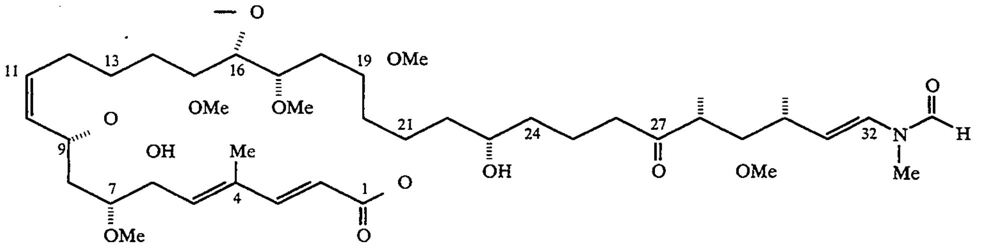

EXAMPLE 6

Tests run on 6-hydroxyscytophycin B which was isolated in accordance with Example 4 above demonstrated that it has the following characteristics:

Form: White amorphous solid.

Empirical Formula: $C_{45}H_{73}NO_{13}$

Molecular Weight: 835. MS (fast-atom bombardment): m/z $(M+K)^+858.5$, $(M+Li)^+842.4$, $(MH-H_2O)^+818.4$.

CD (ethanol): $[\theta]_{297}-550$, $[\theta]_{268}+1500$, $[\theta]_{226}-2920$.

UV$\lambda_{max}$ (ethanol): 261 nm ($\epsilon$23,800) IR (methylene chloride): 3400, 3170, 1690, 1660, 1240, 1115 $cm^{-1}$.

NMR analysis was performed on 6-hydroxyscytophYcin B yielding the data in Table 2.

Table 2

$^1$H NMR: $\delta$ (multiplicity, J in Hz, assignment; nOe's): 5.87 (d, 15.9, H-2; 4-Me), 7.64 (d, 15.9, H-3; H-5 and 17-Ome ), 1.93 (br d, 1.0, 4-Me; H-2 and H-6, 6), 5.93 (br d, 10.0, H-5; H-3, H-7, and 17-OMe), 4.17 (dd, 10.0 and 8.9, H-6; 4-Me and H-8), 3.77 (ddd, 8.9, 10.9, and 1.0, H-7; H-5, H-8, and H-9), 1.26 (ddd, −13.9, 10.9, and 1.5, H-8; H-8'), 1.61 (ddd, −13.9, 9.9, and 1.0, H-8'; H-7, H-8, and H-13), 4.57 (dm, 9.9, H-9; H-7, H-8, H-10, and 17-OMe), 5.64 (dddd, 10.5, 2.7, 2.3, and 1.5, H-10; H-8, H-9, and H-11), 5.79 (ddt, 10.5, 5.3, and 2.2, H-11; H-10, H-12, and H-12'), 1.90 (m, H-12 and H-12'; H-11 and H-13), 3.36 (m, H-13; H-8', H-12, H-12', H-14, H-14', H-15 and H-17), 1.53 (dd, 5.5 and 5.0, H-14 and H-14'; H-13, H-15, and H-16'), 3.89 (t, 5.0, H-15; H-14, H-14'and H-19), 3.35 (s, 15-OMe), 2.68 (d, 5.0, H of CHH' on C-16; H-18), 2.70 (d, 5.0, H' of CHH' on C-16; H-14), 3.76 (dd, 10.3 and 4.0, H-17; H-13, H-18, H-19, and H-20), 3.27 (s, 17-OMe; H-5, H-9, and H-18'), 1.46 (ddd, −13.9, 9.9, and 4.0, H-18; H-16, H-17, and H-18'), 1.94 (m, H-18'; H-18 and 17-OMe), 3.30 (ddd, 9.9, 4.0, and 1.0, H-19; H-15, H-17, and H-21), 3.17 (s, 19-OMe), 2.08 (ddq, 10.0, 7.0, and 1.0, H-20; H-17, 2O-OMe, and 17-OMe), 0.85 (d, 7.0, 2O-Me; H-20), 5.21 (dd, 10.0 and 1.0, H-21; H-19, H-22, 19-OMe, 2O-Me, 23-OH, and $H_2O$), 1.95 (ddq, 9.9, 6.9, and 1.0, H-22; H-21), 0.87 (d, 6.9, 22-Me; H-24), 3.03 (ddd, 9.9, 4.4, and 2.0, H-23; H-22, 22-Me, and 24-Me), 4.00 (d, 4.4, 23-OH; H-21), 1.69 (m, H-24; H-26', 22-Me, and 24-Me), 0.97 (d, 6.4, 24-Me; H-24 and H-26), 1.38 (m, H-25; H-24, H-25, and H-26), 1.74 (m, H-25'; H-24, H-25, and H-26), 2.55 and 2.57 (m, H-26 and H-26'; H-25, H-25', H-28, 24-Me, and 28-Me), 2.75 (dq, 9.5 and 6.5, H-28; H-26, H-26', and 28-Me), 0.90 (d, 6.5, 28-Me; H-26, H-28, and H-31A), 3.27 (dd, 9.5 and 2.5, H-29; H-30A and 3O-Me), 3.29 (s, 29-OMe), 2.46 (ddl, 8.9, 2.5, and 7.0, H-30A; H-29, 28-Me, and 3O-Me), 2.52 (m, H-30B), 1.13 (d, 7.0, 3O-Me; H-29 and H-30A), 5.10 (dd, 13.9 and 8.9, H-31A; N-MeA), 5.16 (dd, 14.4 and 8.9, H-31B; N-MeB), 6.77 (d, 13.9, H-32A; N-CHO A), 7.09 (d, 14.4, H-32B), 2.97 (br s, N-Me A; H-31 A), 3.09 (br s, N-Me B; H-31 B and N-CHO B), 8.34 (s, N-CHO A; H-32 A), 8.10 (s, N-CHO B; Me on N B).

$^{13}C$ NMR: $\delta_c$ (multiplicity, position) 169.27 (s, C-1), 117.84 (d, C-2), 151.65 (d, C-3), 136.91 (s, C-4), 12.64 (q, 4-Me), 141.36 (d, C-5), 72.21 (d, C-6), 72.67 (d, C-7), 37.45 (t, C-8), 70.64 (d, C-9), 131.36 (d, C-10), 125.27 (d, C-11), 31.98 (t, C-12), 66.98 (d, C-13), 36.45 (t, C-14), 78.32 (d, C-15), 57.55 (q, 15-OMe), 61.35 (s, C-16), 46.96 (t, $CH_2$ on C-16), 76.27 (d, C-17), 53.80 (q, 17-OMe), 28.21 (t, C-18), 77.56 (d, C-19), 57.74 (q, 19-OMe), 38.23 (d, C-20), 9.30 (q, 2O-Me), 76.95 (d, C-21), 38.04 (d, C-22), 9.30 (q, 22-Me), 76.61 (d, C-23), 33.93 (d, C-24), 18.29 (q, 24-Me), 22.83 (t, C-25), 42.15 (t, C-26), 213.97 (s, C-27), 49.53 (d, C-28), 13.68 (q, 28-Me), 88.38 (d, C-29), 61.19 (q, 29-OMe), 38.42 (d, C-30A), 38.07 (d, C-30B), 19.65 (q, 3O-Me), 111.21 (d, C-31A), 113.25 (d, C-31B), 130.25 (d, C-32A), 125.56 (d, C-32B), 27.24 (q, N-Me A), 33.04 (q, N-Me B), 162.90 (d, N-CHO A), 161.65 (d, N-CHO B).

Based on the NMR data shown in Table 2, 6-hydroxyscytophycin. B is believed to have the following chemical structure:

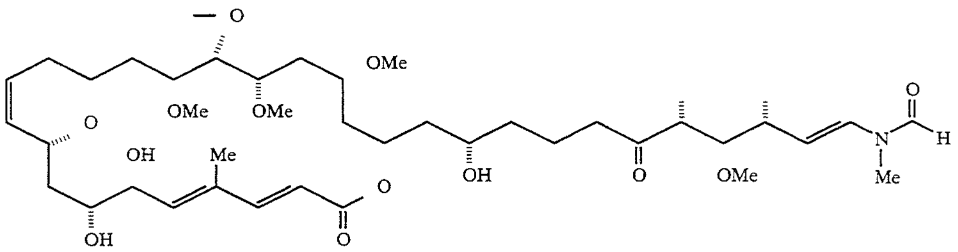

EXAMPLE 7

Tests run on 19-O-demethylscytophycin C which was isolated in accordance with Examples 3 and 4 above, demonstrated that it has the following characteristics:

Chemical Form: White amorphous solid

Empirical Formula: $C_{44}H_{73}NO_{11}$.

Molecular Weight: 791. MS (fast-atom bombardment): m/z $(M+K)^+$830.5, $(M+Na)^+$814.5, $(M+Li)^+$798.6, $(MH-H_2O)^+$774.5.

CD (ethanol): $[\theta]_{297}-380$, $[\theta]_{268}+1500$, $[\theta]_{226}-2600$.

UV$\lambda_{max}$ (ethanol): 261 nm ($\epsilon$21,900)

IR (methylene chloride): 3400, 3170, 1690, 1660, 1240, 1115 $cm^{-1}$.

An NMR analysis was performed on 19-O-demethylscytophycin C, producing the results reported in Table 3.

Table 3

$^1H$ NMR: $\delta$ (multiplicity, J in Hz, assignment) 5.73 (d, 15.8, H-2), 7.47 (d, 15.8, H-3), 1.82 (br s, 4-Me), 6.07 (dd, 10.2 and 5.0, H-5), 2.48 (ddd, −16.2, 10.2, and 10.0, H-6), 2.52 (ddd, −16.2, 5.0 and 3.1, H-6'), 4.04 (ddt, 3.1, 1.2, and 10.0, H-7), 1.20 (ddd, -14.7, 10.0, and 1.8, H-8), 1.74 (ddd, −14.7, 9.8, and 1.2, H-8'), 4.50 (dm, 9.8, H-9), 5.65 (ddt, 10.5, 2.9, and 1.7, H-10), 5.74 (ddt, 10.5, 2.1, and 4.0, H-11), 1.85 (m, H-12 and H-12'), 3.29 (m, H-13), 1.55 (ddd, −14.7, 10.0, and 1.5, H-14), 1.66 (ddd, −14.7, 8.2, and 2.0, H-14'), 3.60 (dt, 8.2 and 1.7, H-15), 3.28 (s, 15-OMe), 1.85 (ddq, 8.0, 1.7, and 6.7, H-16), 0.83 (d, 6.7, 16-Me), 3.36 (ddd, 10.2, 8.0, and 2.7, H-17), 3.34 (s, 17-OMe), 1.75 (ddd, −14.2, 10.2, and 1.5, H-18), 1.85 (ddd, −14.2, 6.0, and 2.7, H-18'), 4.19 (br ddd, 6.0, 2.0, and 1.5, H-19), 3.35 (br d, 2.0, 19-OH), 1.90 (ddq, 10.4, 1.0, and 7.3, H-20), 0.92 (d, 7.3, 2O-Me), 5.12 (br d, 10.4, H-21), 1.95 (ddq, 9.9, 1.0, and 6.9, H-22), 0.84 (d, 6.9, 22-Me), 3.03 (ddd, 9.9, 4.4, and 2.0, H-23), 4.35 (d, 4.4, 23-OH), 1.69 (m, H-24), 0.97 (d, 6.4, 24-Me), 1.38 (m, H-25), 1.76 (m, H-25'), 2.50 (m, H-26), 2.55 (m, H-26'), 2.75 (dq, 9.5 and 6.5, H-28), 0.92 (d, 6.5, 28-Me), 3.27 (dd, 9.5 and 2.5, H-29), 3.30 (s, 29-OMe), 2.46 (ddq, 8.9, 2.5, and 7.0, H-30A), 2.25 (m, H-30B), 1.13 (d, 7.0, 3O-Me), 5.11 (dd, 13.9 and 8.9, H-31A), 5.18 (dd, 14.4 and 8.9, H-31B), 6.78 (d, 13.9, H-32A), 7.09 (d, 14.4, H-32B), 2.98 (br s, N-Me A), 3.10 (br s, N-Me B), 8.35 (s, N-CHO A), 8.09 (s, N-CHO B).

$^{13}C$-NMR: $\delta_c$ (multiplicity, position) 169.89 (s, C-1), 116.54 (d, C-2), 150.83 (d, C-3), 135.01 (s, C-4), 12.31 (q, 4-Me), 139.37 (d, C-5), 39.46 (t, C-6), 68.17 (d, C-7), 40.63 (t, C-8), 70.33 (d, C-9), 131.67 (d, C-10), 125.50 (d, C-11), 32.43 (t, C- 12), 65.03 (d, C-13), 39.25 (t, C-14), 77.92 (d, C-15), 56.58 (q, 15-OMe), 40.28 (d, C-16), 9.27 (q, 16-Me), 82.50 (d, C-17), 56.08 (q, 17-OMe), 35.78 (t, C-18), 65.88 (d, C-19), 43.14 (d, C-20), 9.41 (q, 2O-Me), 76.97 (d, C-21), 38.07 (d, C-22), 9.32 (q, 22-Me), 76.49 (d, C-23), 33.97 (d, C-24), 18.39 (q, 24-Me), 22.78 (t, C-25), 42.18 (t, C-26), 214.07 (s, C-27), 49.54 (d, C-28), 13.67 (q, 28-Me), 88.34 (d, C-29), 61.17 (q, 29-OMe), 38.42 (d, C-30A), 38.23 (d, C-30B), 19.67 (q, 3O-Me), 111.14 (d, C-31A), 113.21 (d, C-31B), 130.24 (d, C-32A), 125.52 (d, C-32B), 27.22 (q, N-Me A), 33.04 (q, N-Me B), 162.88 (d, N-CHO A), 161.64 (d, N-CHO B).

Based on the NMR data shown in Table 3, 19-O-demethylscytophycin C is believed to have the following chemical structure:

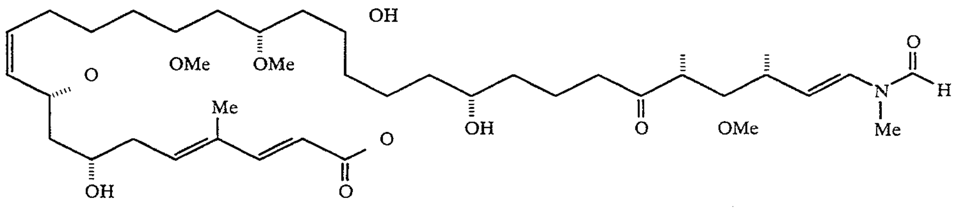

EXAMPLE 8

Tests run on 6-hydroxy-7-O-methylscytophycin E which was isolated in accordance with Examples 3 and 4, determined that it has the following characteristics:

Chemical Form: White amorphous solid

Empirical Formula: $C_{46}H_{77}N)_{13}$.

Molecular Weight: 851. MS (fast-atom bombardment): m/z $(M+K)$:+890.6, $(M+Na)$+874.6, (MH-$H_2O$)+834.5, (MH-2$H_2O$)+816.6.

CD (ethanol): $[\theta]_{297}-350$, $[\theta]_{268}+2400$, $[\theta]_{226}-3200$.

UV$\lambda_{max}$ (ethanol): 261 nm ($\epsilon$27,900)

IR (methylene chloride): 3400, 3180, 1690, 1665, 1240, 1125 $cm^{-1}$.

NMR analysis was performed on 6-hydroxy-7-O-methylscytophycin E yielding the data reported in Table 4.

Table 4

$^1$H NMR $\delta$ (multiplicity, J in Hz, assignment; nOe's): 5.83 (d, 15.8, H-2; 4-Me and 17-OMe), 7.57 (d, 15.8, H-3; H-5, H-19, and 17-OMe), 1.86 (br d, 1.0, 4-Me; H-2, H-6, and 17-OMe ), 6.02 (br d, 8.9, H-5; H-3, H-6, and H-7), 4.39 (t, 8.9, H-6; 4-Me, and 7-OMe), 4.16 (br s, OH on C-6), 3.42 (ddd, 11.0, 8.9, and 2.0, H-7; H-5, H-8', and H-9), 3.57 (s, 7-OMe; H-6 and 4-Me), 1.30 (ddd, −13.8, 11.0, and 3.0, H-8; H-8' and H-9), 1.57 (ddd, −13.8, 9.5, and 2.0, H-8'; H-7, H-8, and H-13), 4.40 (dm, 9.5, H-9; H-7 and H-8), 5.66 (ddt, 10.3, 2.8, and 1.7, H-10; H-9 and H-11), 5.76 (dddd, 10.3, 5.4, 2.9, and 2.5, H-11; H-10), 1.87 (m, H-12; CH' on 16 and H-13), 1.91 (m, H-12'), 3.26 (br ddd, 10.3, 8.9, and 3.4, H-13; H-8' and H-12), 1.75 (br dd, −13.8 and 10.3, H-14; 15-OMe), 1.88 (m, H-14'), 3.87 (br d, 8.9, H-15; H-13, H-16, 15-OMe, and 17-OMe), 3.36 (s, 15-OMe; H-14 and H-15), 1.51 (br dd, 9.8 and 2.4, H-16; H-15, 17-OMe, and 19-OMe), 3.70 (br d, 11.7, CH on C-16; H-12, H-16, and CH' on 16), 3.77 (dd, 11.7 and 2.4, CH' on C-16; H-16 and CH on 16), 3.67 (ddd, 9.8, 4.9, and 4.4, H-17; H-18 and H-18'), 3.39 (s, 17-OMe; H-3, H-15, H-16, and H-20), 1.98 (m, H-18 and H-18'; H-17), 3.72 (br t, 4.9, H-19; H-3, H-21, 17-OMe, and 19-OMe), 3.14 (s, 19-OMe; H-16, H-19, H-20, H-21, 2O-Me), 2.04 (ddq, 9.9, 1.0, and 6.9, H-20; 17-OMe, 19-OMe, and 2O-Me), 0.94 (d, 6.9, 2O-Me; H-20, H-21, and 19-OMe), 5.15 (dd, 9.9 and 0.9, H-21; H-19, H-22, H-23, 19-OMe, 23 -OH, 20 -Me, and $H_2O$ ) 1.97 (ddq, 9.9, 0.9, and 6.9, H-22; H-21 and 22-Me), 0.84 (d, 6.9, 22-Me; H-22 and H-23), 3.07 (ddd, 9.9, 4.0, and 1.9, H-23; H-21 and H-25'), 4.09 (d, 4.0, 23-OH; H-21, 22-Me, and 24-Me), 1.68 (dddq, 9.9, 4.0, 1.9, and 6.9, H-24), 0.97 (d, 6.9, 24-Me; H-23 and H-26), 1.37 (m, H-25; H-25' and 24-Me), 1.75 (m, H-25'; H-23, H-25, H-26, 22-Me, and 24-Me), 2.50 and 2.55 (m, H-26 and H-26'; H-25, H-28, and 24-Me), 2.76 (dq, 9.4 and 6.9, H-28; H-26', 29-Ome, and 28-Me), 0.90 (d, 6.9, 28-Me; H-28, H-29, H-30A, and H-30B), 3.28 (dd, 9.4 and 2.9, H-29; H-28, H-30A, H-30B, 28-Me, and 3O-Me), 3.30 (s, 29-OMe; H-29), 2.46 (dq, 2.9 and 7.4, H-30A; H-29 , 28-Me, and 3O-Me), 2.47 (dq, 2.9 and 7.4, H-30B; 28-Me and 30-Me ), 1.13 (d, 7.4, 30-Me; H-29, H-30A, and H-30B), 5.10 (dd, 14.3 and 9.3, H-31A; N-Me A), 5.15 (dd, 14.7 and 9.3, H-31B) 6.76 (d, 14.3, H-32A; N-CHO A), 7.09 (d, 14.7, H-32B), 2.97 (s, N-Me A; H-31 A), 3.09 (s, N-Me B; N-CHO B), 8.35 (s, N-CHO A; H-32 A), 8.10 (s, N-CHO B; Me on N B).

$^{13}$C NMR $\delta_c$ (multiplicity, position): 169.06 (s, C-1), 117.77 (d, C-2), 151.37 (d, C-3), 135.05 (s, C-4), 12.72 (q, 4-Me), 142.70 (d, C-5), 72.38 (d, C-6), 82.62 (d, C-7), 60.51 (q, 7-OMe), 36.33 (t, C-8), 70.41 (d, C-9), 130.98 (d, C-10), 124.86 (d, C-11), 32.27 (t, C-12), 65.45 (d, C-13), 38.91 (t, C-14), 79.51 (d, C-15), 57.01 (q, 15-OMe), 47.61 (d, C-16), 59.67 (t, $CH_2OH$ on C-16), 78.28 (d, C-17), 55.76 (q, 17-OMe), 33.93 (t, C-18), 76.80 (d, C-19), 58.77 (q, 19-OMe), 42.60 (d, C-20), 9.76 (q, 2O-Me), 77.19 (d, C-21), 38.56 (d, C-22), 9.22 (q, 22-Me), 76.51 (d, C-23), 34.05 (d, C-24), 18.28 (q, 24-Me), 22.76 (t, C-25), 42.11 (t, C-26), 213.97 (s, C-27), 49.51 (d, C-28), 13.65 (q, 28-Me), 88.33 (d, C-29), 61.12 (q, 29-OMe), 38.20 (d, C-30A), 38.42 (d, C-30B), 19.60 (q, 3O-Me), 111.17 (d, C-31A), 113.22 (d, C-31B), 130.19 (d, C-32A), 125.51 (d, C-32B), 27.21 (q, N-Me A), 33.00 (q, N-Me B), 162.82 (d, N-CHO A), 161.57 (d, N-CHO B) .

Based on the NMR data shown in Table 4, 6-hydroxy-7-O-methylscytophycin E is believed to have the following chemical structure:

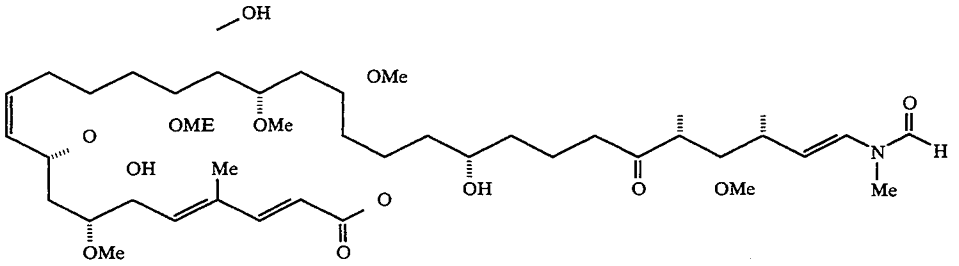

Inhibitor Applications for New Scytophycins

EXAMPLE 9

Tolytoxin and the other new scytophycin compounds are potent anticancer and antifungal agents. The cytotoxicity of tolytoxin and other new scytophycin compounds was determined using a cell proliferation assay, which tested the effect of the compounds on increases in cell numbers.

Cell lines were grown in plastic dishes (Falcon) in Eagle's basal medium supplemented with 5% newborn calf serum (KB), Fisher's medium supplemented with 10% horse serum (L1210), Dulbecco's modified Eagle's medium supplemented with 5% heat-inactivated fetal calf serum (LoVo), minimal essential medium supplemented with 2% heat-inactivated chicken serum (HEp-2), RPMI-1640 supplemented with 10% heat-inactivated fetal calf serum (T-47D, COLO-201) or 20% heat-inactivated fetal calf serum (HL-60, KATO-III), or McCoy's 5A supplemented with 10% heat-inactivated fetal calf serum (HBL-100). All cell culture media were supplemented with 50 $\mu$g/ml gentamycin sulfate. The cultures were incubated at 37° C. in a humidified atmosphere containing 5% carbon dioxide.

Cultures were exposed to graded concentrations of tolytoxin and reincubated for 72 hours in the presence of tolytoxin. Three dishes were used for each treatment. Cell numbers were determined by hemacytometer counts. The $IC_{50}$ for each cell line was determined by plotting the logarithm of the tolytoxin concentration versus growth (cell number as a percentage of the control) of the treated cells.

The toxicity of tolytoxin to various animal and human cell lines in tissue culture is shown in Table 5.

TABLE 5

Cytotoxicity of Tolytoxin

| Cell Line | ATCC Number | Tumor Type | $IC_{50}$ (nM) |
|---|---|---|---|
| L1210 | CCL 219 | Murine Leukemia | 3.9 |
| LoVo | CCL 229 | Human Adenocarcinoma | 8.4 |
| KB | CCL 17 | Human Epidermoid Carcinoma | 5.3 |
| HEp-2 | CCL 23 | Human Epidermoid Carcinoma | 2.3 |
| HL-60 | CCL 240 | Human Promyelocytic Leukemia | 4.8 |
| HBL-100 | HTB 124 | Human Breast | 2.4 |
| T47-D | HTB 133 | Human Ductal Carcinoma | 4.9 |
| COLO-201 | CCL 224 | Human Colon Adenocarcinoma | 0.52 |
| KATO-III | HTB 103 | Human Gastric Carcinoma | 0.78 |

EXAMPLE 10

The other new scytophycin compounds are also potent cytotoxins. For example, the $IC_{50}$ of the scytophycins against KB human epidermoid carcinoma, LoVo human adenocarcinoma, and L1210 murine leukemia were determined using the cell proliferation assay described for tolytoxin. The results of these tests are summarized In Table 6.

TABLE 6

Effect of the Scytophycins on Growth of Mammalian Cells

| Compound | $IC_{50}$ (nM) KB | L1210 | LoVo |
|---|---|---|---|
| 6-Hydroxyscytophycin B | 3.6 | 11.0 | 8.2 |
| 19-O-demethylscytophycin C | 9.2 | 12.5 | 2.9 |
| 6-Hydroxy-7-O-methylscytophycin E | 12.0 | 6.6 | 8.0 |

EXAMPLE 11

The cytotoxicity of the new scytophycins also extends to cells normally resistant to a variety of antineoplastic drugs.

Human ovarian carcinoma cells (SKOV3) and a subline made multi-drug resistant by slowly increasing vinblastine in the culture medium over the course of many passages (SKVLB) were grown in Earle's basal medium (BME) containing 10% fetal calf serum. The SKVLB cells were maintained in the presence of 1 82 g/mL vinblastine. The multi-drug resistant cell line is resistant to adriamycin, vinblastine, actinomycin D, and colchicine.

Cell proliferation was estimated by measurement of protein content of the cultured cells, as described by Skehan et al. (1990). Cells were plated into 24-well plates at approximately 10% confluency in BME and were allowed to attach and recover for at least 24 hours. The cells were then treated with the scytophycins or appropriate control for 48 hours. After the incubation, the medium was removed from each well and cells fixed by addition of 10% (w/v) trichloroacetic acid (TCA) (4° C.). The cells were incubated at 4° C. for one hour and then washed five times with water to remove TCA. The TCA-fixed cells were then stained for 30 minutes with 0.4% (w/v) sulforhodamine B prepared in 1% acetic acid. Following the staining, the cell layers were washed four times with 1% acetic acid. The cell layer was dissolved in 10 mM unbuffered tris-hydroxymethylaminomethane base. Absorbance of the solution was determined at 564 nm. Antiproliferative activity is manifested as decreased production of cellular protein.

Table 7 shows the effect of the scytophycins on proliferation in SKOV3 and SKVLB cell lines.

TABLE 7

Effect of the Scytophycins on Multi-Drug Resistant Cell Lines

| Compound | $IC_{50}$ (nM) SKOV3 | SKVLB | Fold-Resistance |
|---|---|---|---|
| Adriamycin | 400 | >100,000 | >250 |
| Vinblastine | 1 | 10,000 | 10,000 |
| Cytochalasin B | 5,000 | 30,000 | 6 |
| Tolytoxin | 25 | 25 | 1 |
| 6-hydroxyscytophycin B | 50 | 150 | 3 |
| 19-O-demethylscytophycin C | 25 | 25 | 1 |
| 6-hydroxy-7-O-methylscytophycin E | 100 | 300 | 3 |

EXAMPLE 12

The new scytophycins are also useful as antifungal agents. Antimicrobial activity was determined by the agar dilution method. Tolytoxin was dissolved in 95% ethanol for addition to cooled, molten agar. Nystatin was solubilized in DMSO and diluted in distilled water. Appropriate solvent controls were also prepared. Fungal cultures were grown on Saboraud dextrose agar. Assay plates were incubated for 48 hours post-inoculation. Yeasts and filamentous fungi were incubated at 25° C. Minimum Inhibitory Concentrations (MIC) were estimated visually as the lowest concentration of drug showing no growth or significantly reduced growth relative to the controls.

Antifungal activity of tolytoxin is shown in Table 8.

TABLE 8

Antifungal Activity of Tolytoxin

| Organism | MIC (nM) Tolytoxin | Nystatin |
|---|---|---|
| *Alternaria alternata* 1715 | 4 | 0.5 |
| *Aspergillus oryzae* | 0.5 | 0.5 |
| *Bipolaris incurvata* 2118 | 2 | 0.25 |
| *Calonectria critalarae* 1809 | 2 | 0.25 |
| *Candids albicans* A26 | 8 | 1 |
| *Colletotrichum coccodes* 1809 | 4 | 0.25 |
| *Penicillium notatum* | 0.25 | 0.125 |
| *Phyllosticta capitalensis* 689-5 | 0.5 | 0.125 |
| *Phytophthora nicotianae* H729 | 4 | 1 |
| *Rhizoctonia solani* 1165 | 0.25 | 0.0625 |
| *Saccharomyces cerevisae* | 4 | 1 |
| *Sclerotium rofsii* 2133 | 1 | 0.125 |
| *Thielaviopsis paradoxa* 1215 | 1 | 0.5 |
| *Trichophyton mentagrophytes* A23 | 8 | 0.5 |

EXAMPLE 13

The other new scytophycin compounds are also useful as antifungal agents, as is shown indicated in Table 9. Activity was determined using the method described above for tolytoxin.

TABLE 9

| Antifungal Activity of Scytophycins | | | |
|---|---|---|---|
| | $IC_{50}$ (nM) Compound Number | | |
| Organism | 2 | 3 | 4 |
| *Candida albicans* A26 | 200 | 128 | 64 |
| *Sclerotium rofsii* 2133 | 16 | 4 | 16 |
| *Phytophthora nicotianae* H729 | 64 | 8 | 16 |
| *Saccharomyces cerevisae* | 100 | 64 | 64 |
| *Thielaviopsis paradoxa* 1215 | 32 | 16 | 32 |

Key to compounds:
2. 6-Hydroxyscytophycin B
3. 19-O-demethylscytophycin C
4. 6-Hydroxy-7-O-methylscytophycin E

EXAMPLE 14

In view of the cytotoxic effects observed with the new scytophycins, an experiment was performed to determine the toxicity level in an animal model. Various doses of tolytoxin were administered to Swiss Webster mice by the intraperitoneal route. The $LD_{50}$ of tolytoxin in Swiss Webster mice was determined to be approximately 1.5 mg/kg.

Effects on Cell Nuclei

EXAMPLE 15

The following procedure employs new scytophycins to produce polynucleated mammalian cells. Murine leukemia (L1210) cells at a density of $1\times10^5$ cells/mL were treated with tolytoxin for periods ranging from 4 to 24 hours. Tolytoxin or the appropriate vehicle as a control was added in a volume of not more than 4.2 $\mu$L per 10 mL of cell suspension. The cell suspension was incubated at 37° C. in a humidified atmosphere of 95% air, 5% carbon dioxide. At the conclusion of the incubation, the cultures were chilled on ice and centrifuged at 200×g (gravity) for 10 minutes. The pelleted cells were fixed in 70% ethanol: 30% water for 1 hour. Aliquots of the fixed cell suspensions were washed twice with 0.01M phosphate buffered saline, pH 7.2–7.4. The cells were resuspended at approximately $1\times10^6$/mL in modified Krishan's reagent (Krishan, 1975) containing 0.005% propidium iodide, ribonuclease A at 50 units/mL, 0.1% sodium citrate, and 0.3% Nonidet P-40. Following a 30 minute incubation at 4° C. the cell suspensions were passed 4 times through a 26-gauge needle before analysis on a Coulter Epics C flow cytometer, equipped with an Innova 90 argon laser tuned at 488 nm and set at 200 milliwatts. The fluorescence of 10,000 cells was used to generate the DNA histograms.

Results of the analysis are depicted in FIG. 3. At each time point examined, control (untreated) cell populations showed similar cell distributions among the $G_oG_1$ (2 C diploid DNA content), S and $G_2M$ (4 C DNA content) cell cycle phases [FIG. 3, Control]. Cell cultures treated with 10 nM tolytoxin for time periods ranging from 4 to 24 hours showed a gradual increase in the. proportion of cells in the $G_2M$ phase [FIG. 3, treatment times as indicated]. By 16 hours approximately $\frac{1}{3}$ of the cells had DNA contents greater than 4C. These changes were reflected by the increasing numbers of multinucleated cells observed by microscopy.

EXAMPLE 16

In the following procedure new scytophycins were employed to cause nuclear protrusion in mammalian cells. Human epidermoid carcinoma (KB) cells were plated on plastic tissue-culture dishes in Dulbecco's modified Eagle's medium at $1\times10^5$ cells per 60 mm dish. The cell cultures were incubated overnight at 37° C. in a humidified atmosphere of 95% air and 5% carbon dioxide to allow the cells to settle and become attached. Following the incubation, tolytoxin or the appropriate vehicle control was added in a volume of not more than 35 $\mu$L per 5 mL of culture medium. After an additional incubation period ranging from 1 to 4 hours, the culture medium was removed and the cell layer washed twice with phosphate-buffered saline (PBS), pH 7.2. The washed cell layer was stained for 15 minutes with 0.01% acridine orange in PBS. Following staining, the cell suspension was washed for 15 minutes with two changes of PBS to remove unbound stain and photographed on a Zeiss IM-35 photomicroscope equipped with brightfield and epifluorescence optics.

Figure 4A:
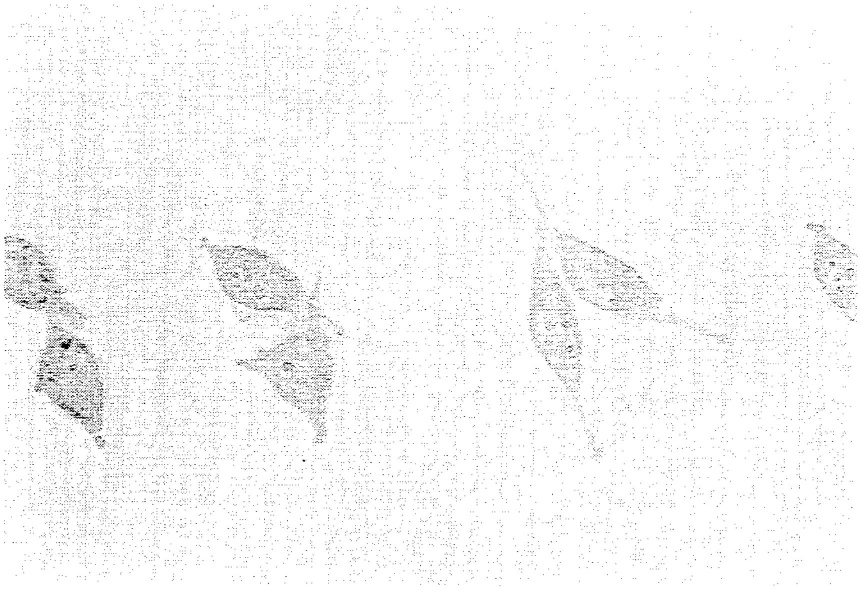
FIG. 4A is a brightfield micrograph of normal human epidermoid carcinoma ("KB") cells.
Figure 4B:
FIG. 4B is a fluorescence micrograph of normal KB cells showing the light emitted from acridine orange which is bound to the cells' nuclear DNA.
Figure 5:
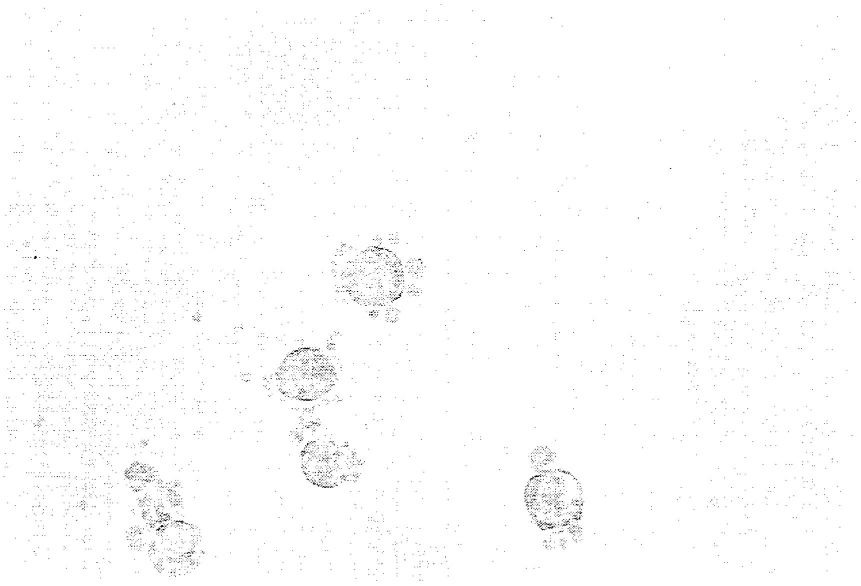
FIG. 5 is a brightfield micrograph of KB cells after tolytoxin treatment to produce fibroblastoid cellular shape and the appearance of blebs or zeioses on the cell surfaces.

FIGS. 4–6 illustrate the ability of the new scytophycins to be used to produce enucleated cells. FIG. 4A shows the normal shape and appearance of the KB cells by brightfield microscopy. FIG. 4B is a micrograph of the light emitted by the acridine orange bound to the DNA of the same cells, illustrating the size, shape and location of the cell nuclei.

FIG. 5 shows the effect of 4 nM tolytoxin on KB cells following an exposure interval of 1 hour. As shown, the cells have lost their normal extended fibroblastoid shape, and the appearance of blebs or zeioses on the cell surface is apparent.

Figure 6A:
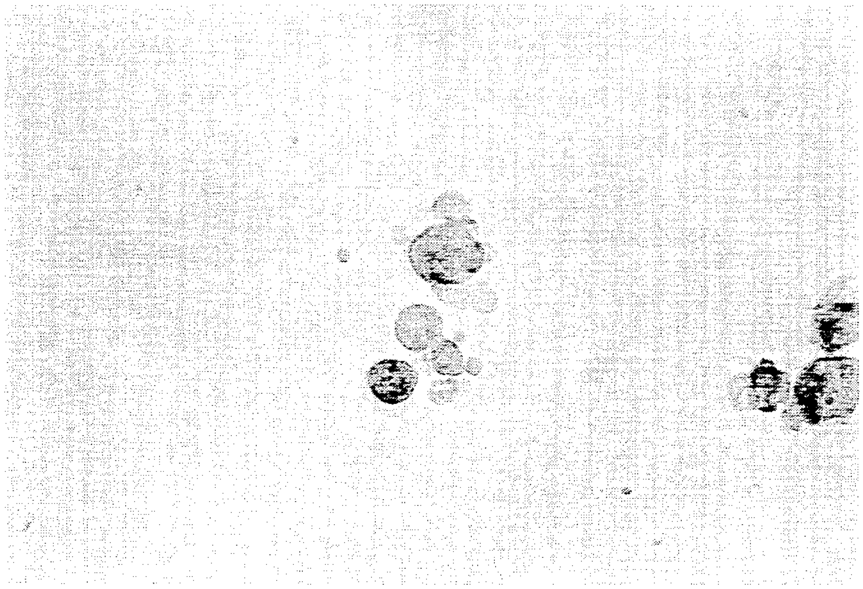
FIG. 6A is a brightfield micrograph of tolytoxin treated KB cells in which the cell nuclei have migrated out of their respective cell bodies.
Figure 6B:
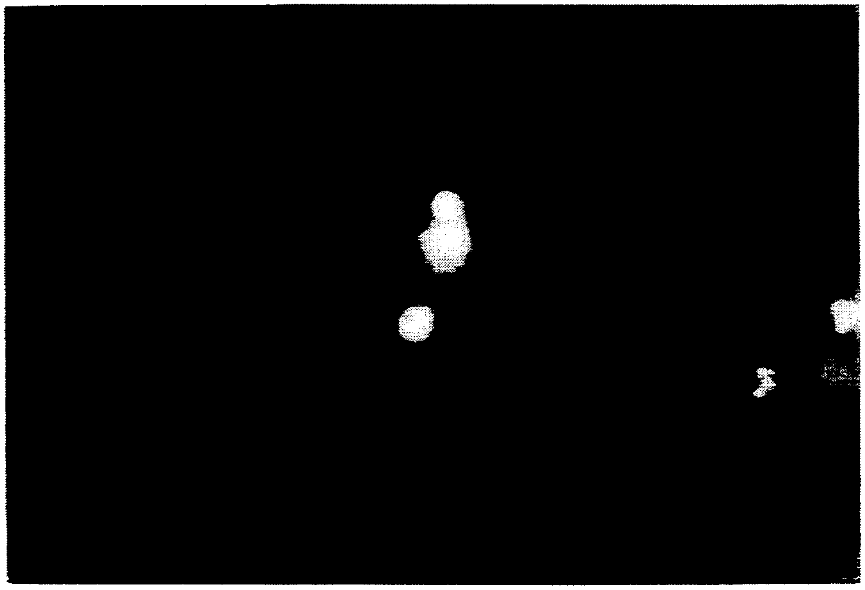
FIG. 6B is a fluorescence micrograph of tolytoxin treated KB cells in which the cell nuclei have migrated out of their respective cell bodies.

FIG. 6 shows the appearance of the KB cells following exposure to 8nM tolytoxin for a period of 4 hours. The cell nucleus has migrated outside the body of the cell and now occupies one of the zeiotic processes. FIG. 6A shows treated cell structures as viewed through a brightfield microscope. FIG. 6B shows the position of migrated cell nuclei in a fluorescence micrograph.

Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the claims.

We claim:

1. A scytophycin compound in accordance with the formula:

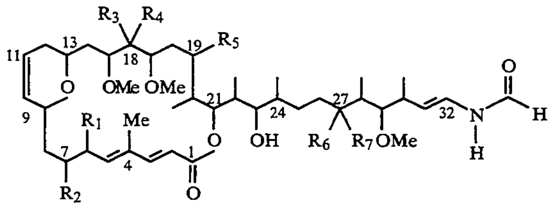

wherein:

$R_1$ is selected from the group consisting of H and X, wherein X is selected from the group consisting of OH, OMe, $O(CH_2)_zMe$, and O—CO—Y, wherein Y is selected from the group consisting of H, $C_nH_{2n+1}$, and Ph, wherein n and z are independently selected integers from 1 to 5;

$R_2$ is X independent of identity of X for $R_1$;

$R_3$ is Me or $CH_2OH$ and $R_4$ is H or OH, or $R_3$ and $R_4$ together are $CH_2O$ (epoxy);

$R_5$ is X independent of identity of X for $R_1$ and $R_2$; and $R_6$ is OH and $R_7$ is H, or $R_6$ and $R_7$ together are O (keto);

with the provisos that:

when $R_1$ is H, $R_2$ is OH and $R_6$ and $R_7$ are O (keto) at least one of the following limitations apply:

$R_3$ and $R_4$ are not $CH_2O$ (epoxy); or $R_3$ is not Me; or $R_5$ is not OMe; and when $R_1$ is H, $R_2$ is OH and $R_6$ is OH at least one of the following limitations apply:

$R_3$ and $R_4$ are not $CH_2O$ (epoxy); or $R_5$ is not OMe.

2. The compound of claim 1 wherein $R_5$ is O (keto).

3. The compound of claim 2 wherein $R_1$ is OH, $R_2$ is OMe, $R_3$ and $R_4$ are $CH_2O$ (epoxy), and $R_5$ is OMe.

4. The compound of claim 2 wherein $R_1$ is OH, $R_2$ is OH, $R_3$ and $R_4$ are $CH_2O$ (epoxy) and $R_5$ is OMe.

5. The compound of claim 2 wherein $R_1$ is H, $R_2$ is OH, $R_3$ is Me, and $R_5$ is OH.

6. The compound of claim 2 wherein $R_1$ is OH, $R_2$ is OMe, $R_3$ is $CH_2OH$, and $R_5$ is OMe.

7. The compound of claim 1 wherein X is selected from the group consisting of OH and OMe.

8. A composition for inhibiting fungal growth comprising:

a compound in accordance with claim 1; and a suitable carrier.

9. The composition of claim 8 wherein the compound is tolytoxin.

* * * * *